(12) United States Patent
Ikeda et al.

(10) Patent No.: US 7,075,098 B2
(45) Date of Patent: Jul. 11, 2006

(54) METHOD OF SELECTING PATTERN TO BE MEASURED, PATTERN INSPECTION METHOD, MANUFACTURING METHOD OF SEMICONDUCTOR DEVICE, PROGRAM, AND PATTERN INSPECTION APPARATUS

(75) Inventors: Takahiro Ikeda, Kanagawa (JP); Daisuke Kawamura, Kanagawa (JP); Hisako Aoyama, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 227 days.

(21) Appl. No.: 10/730,921

(22) Filed: Dec. 10, 2003

(65) Prior Publication Data
US 2004/0155208 A1    Aug. 12, 2004

(30) Foreign Application Priority Data
Dec. 13, 2002    (JP)    ............................. 2002-362298

(51) Int. Cl.
*G01N 21/86*    (2006.01)

(52) U.S. Cl. ............................... 250/559.3; 259/559.33

(58) Field of Classification Search ............. 250/559.3, 250/559.33
See application file for complete search history.

(56) References Cited

U.S. PATENT DOCUMENTS 6,456,736 B1    9/2002  Su et al.
6,788,996 B1 *  9/2004  Shimizu ..................... 700/213

FOREIGN PATENT DOCUMENTS

JP    10-144743    5/1998
JP    2001-274209  10/2001

* cited by examiner

*Primary Examiner*—Que T. Le
(74) *Attorney, Agent, or Firm*—Finnegan, Henderson, Farabow, Garrett & Dunner, L.L.P.

(57) ABSTRACT

A method of selecting a pattern to be measured includes selecting only points from a combination of all factors effecting dimensional fluctuations. For example, fluctuation between wafers, fluctuation in a wafer, and fluctuation in a chip are candidates for measurement points of patterns to be measured. Further, the number of the selected points corresponds to a divisor of the combination of all factors.

20 Claims, 10 Drawing Sheets

FIG. 9

METHOD OF SELECTING PATTERN TO BE MEASURED, PATTERN INSPECTION METHOD, MANUFACTURING METHOD OF SEMICONDUCTOR DEVICE, PROGRAM, AND PATTERN INSPECTION APPARATUS

CROSS REFERENCE TO RELATED APPLICATION

This application claims benefit of priority under 35USC §119 to Japanese Patent Application No. 2002-362298, filed on Dec. 13, 2002, the contents of which are incorporated by reference herein.

BACKGROUND OF THE INVENTION

1. Field of the Invention

The present invention relates to a method of selecting a pattern to be measured, a pattern inspection method, a manufacturing method of a semiconductor device, a program, and a pattern inspection apparatus, for example, to selection and inspection of a fine pattern to be measured in a manufacturing process of a semiconductor device.

2. Related Background Art

In a manufacturing process of a semiconductor device a scanning electron microscope apparatus, for example, a type called a critical dimension scanning electron microscope (CD-SEM) is used to inspect a dimension of a fine pattern. Moreover, an alignment deviation error of a pattern between layers is measured by an alignment deviation inspection apparatus.

Conventionally, a method of selecting a pattern to be measured depends heavily on a sequence of preparation of measurement schedule of a measurement device. In the method, several wafers to be measured are first selected from one lot, a semiconductor chip to be measured is then selected with respect to these wafers, and a measurement portion in the selected chip is defined. Thereafter, a dimension or alignment deviation is measured in the same measurement portion with respect to all the wafers to be measured and all the chips to be measured. As a result, the number of wafers or chips constituting the measurement objects, and the total number of measurement portions in the chip are obtained by integration of these numbers. Therefore, when the wafer number, chip number, and in-chip measurement portions are simultaneously increased, a measurement cost exponentially increases.

As taught by a design of experiment method, this sampling strategy corresponds to a sampling strategy in which all alternate functions among factors such as fluctuations between the wafers and between the chips, and fluctuations in the chip are handled.

However, in actual, it is difficult to handle high-order alternate functions between the factors. Conversely, there has never been provided a factorial design method of performing measurement in which only the alternate functions to be handled are focused. Accordingly, there has never been provided a method of analyzing the fluctuations for each factor from measurement results obtained by the arrangement. Furthermore, in performing such a factorial design, it would have been remarkably difficult to prepare a measurement recipe in the above-described conventional measurement schedule preparation method.

BRIEF SUMMARY OF THE INVENTION

According to a first aspect of the present invention, there is provided a method of selecting a pattern to be measured comprising:

assigning first wafer numbers in order of a process to a wafer group constituted of a plurality of wafers including a semiconductor chip group respectively, the semiconductor chip group having a plurality of chips, each semiconductor chip having a pattern formed thereon in the process;

dividing the wafer group into at least two first sub-groups in accordance with the first wafer numbers, and selecting at least two wafers having serial first wafer numbers from the first sub-groups to assign second wafer numbers to the selected wafers, respectively;

dividing the semiconductor chip group into at least two second sub-groups in accordance with distances between center positions of semiconductor chips on the wafers to which the second wafer numbers have been assigned and center positions of the wafers, selecting at least three semiconductor chips from the second sub-groups, further selecting a chip including the center position of the wafer inside thereof if any, and assigning a chip number to the selected semiconductor chip;

producing a lattice to divide a region in the selected semiconductor chip to which the chip number is assigned into rectangular regions the number of which exceeds the number of regions of at least two rows and two columns, on the basis of in-chip coordinates, selecting at least four lattice points from the lattice points of the lattice, selecting a pattern in the vicinity of the selected lattice points from the pattern formed on the wafer as only one candidate measurement point with respect to the lattice points, and assigning a candidate measurement point number to the candidate measurement point; and defining only some of the candidate measurement points to which the candidate measurement point numbers have been assigned as first measurement points to be actually measured based on a fractional factorial design for each of the respective semiconductor chips to which the chip numbers have been assigned.

According to a second aspect of the present invention, there is provided a pattern inspection method comprising:

assigning first wafer numbers in order of a process to a wafer group constituted of a plurality of wafers including a semiconductor chip group respectively, the semiconductor chip group having a plurality of chips, each semiconductor chip having a pattern formed thereon in the process;

dividing the wafer group into at least two first sub-groups in accordance with the first wafer numbers, and selecting at least two wafers having serial first wafer numbers from the first sub-groups to assign second wafer numbers to the selected wafers, respectively;

dividing the semiconductor chip group into at least two second sub-groups in accordance with distances between center positions of semiconductor chips on the wafers to which the second wafer numbers have been assigned and center positions of the wafers, selecting at least three semiconductor chips from the second sub-groups, further selecting a chip including the center position of the wafer inside thereof if any, and assigning a chip number to the selected semiconductor chip;

producing a lattice to divide a region in the selected semiconductor chip to which the chip number is assigned into rectangular regions the number of which exceeds the number of regions of at least two rows and two columns, on the basis of in-chip coordinates, selecting at least four lattice points from the lattice points of the lattice, selecting a pattern in the vicinity of the selected lattice points from the pattern formed on the wafer as only one candidate measurement point with respect to the lattice points, and assigning a candidate measurement point number to the candidate measurement point;

defining only some of the candidate measurement points to which the candidate measurement point numbers have been assigned as first measurement points to be actually measured based on a fractional factorial design for each of the respective semiconductor chips to which the chip numbers have been assigned;

preparing a measurement schedule and actually executing measurement to the defined measurement points;

executing an analysis of variance from obtained measurement results on the basis of the fractional factorial design; and changing the measurement schedule on the basis of the result of the analysis of variance.

According to a third aspect of the present invention, there is provided a pattern inspection method using a measurement device, said method comprising:

assigning first wafer numbers in order of a process to a wafer group constituted of a plurality of wafers including a semiconductor chip group respectively, the semiconductor chip group having a plurality of chips, each semiconductor chip having a pattern formed thereon in the process;

dividing the wafer group into at least two first sub-groups in accordance with the first wafer numbers, and selecting at least two wafers having serial first wafer numbers from the first sub-groups to assign second wafer numbers to the selected wafers, respectively;

dividing the semiconductor chip group into at least two second sub-groups in accordance with distances between center positions of semiconductor chips on the wafers to which the second wafer numbers have been assigned and center positions of the wafers, selecting at least three semiconductor chips from the second sub-groups, further selecting a chip including the center position of the wafer inside thereof if any, and assigning a chip number to the selected semiconductor chip;

producing a lattice to divide a region in the selected semiconductor chip to which the chip number is assigned into rectangular regions the number of which exceeds the number of regions of at least two rows and two columns, on the basis of in-chip coordinates, selecting at least four lattice points from the lattice points of the lattice, selecting a pattern in the vicinity of the selected lattice points from the pattern formed on the wafer as only one candidate measurement point with respect to the lattice points, and assigning a candidate measurement point number to the candidate measurement point;

defining only some of the candidate measurement points to which the candidate measurement point numbers have been assigned as first measurement points to be actually measured based on a fractional factorial design for each of the respective semiconductor chips to which the chip numbers have been assigned; and actually measuring a standard pattern prepared beforehand a predetermined times using the measurement equipment, prior to an actual measurement to the defined measurement point to evaluate reliability of the measurement device.

According to a fourth aspect of the present invention, there is provided a manufacturing method of a semiconductor device using a pattern inspection method, said pattern inspection method comprising:

assigning first wafer numbers in order of a process to a wafer group constituted of a plurality of wafers including a semiconductor chip group respectively, the semiconductor chip group having a plurality of chips, each semiconductor chip having a pattern formed thereon in the process;

dividing the wafer group into at least two first sub-groups in accordance with the first wafer numbers, and selecting at least two wafers having serial first wafer numbers from the first sub-groups to assign second wafer numbers to the selected wafers, respectively;

dividing the semiconductor chip group into at least two second sub-groups in accordance with distances between center positions of semiconductor chips on the wafers to which the second wafer numbers have been assigned and center positions of the wafers, selecting at least three semiconductor chips from the second sub-groups, further selecting a chip including the center position of the wafer inside thereof if any, and assigning a chip number to the selected semiconductor chip;

producing a lattice to divide a region in the selected semiconductor chip to which the chip number is assigned into rectangular regions the number of which exceeds the number of regions of at least two rows and two columns, on the basis of in-chip coordinates, selecting at least four lattice points from the lattice points of the lattice, selecting a pattern in the vicinity of the selected lattice points from the pattern formed on the wafer as only one candidate measurement point with respect to the lattice points, and assigning a candidate measurement point number to the candidate measurement point;

defining only some of the candidate measurement points to which the candidate measurement point numbers have been assigned as first measurement points to be actually measured based on a fractional factorial design for each of the respective semiconductor chips to which the chip numbers have been assigned;

preparing a measurement schedule and actually executing measurement to the defined measurement points;

executing an analysis of variance from obtained measurement results on the basis of the fractional factorial design; and changing the measurement schedule on the basis of the result of the analysis of variance.

According to a fifth aspect of the present invention, there is provided a program which allows a computer to implement a method of selecting a pattern to be measured, said selection method comprising:

assigning first wafer numbers in order of a process to a wafer group constituted of a plurality of wafers including a semiconductor chip group respectively, the semiconductor chip group having a plurality of chips, each semiconductor chip having a pattern formed thereon in the process;

dividing the wafer group into at least two first sub-groups in accordance with the first wafer numbers, and selecting at least two wafers having serial first wafer numbers from the first sub-groups to assign second wafer numbers to the selected wafers, respectively;

dividing the semiconductor chip group into at least two second sub-groups in accordance with distances between center positions of semiconductor chips on the wafers to which the second wafer numbers have been assigned and center positions of the wafers, selecting at least three semiconductor chips from the second sub-groups, further selecting a chip including the center position of the wafer inside thereof if any, and assigning a chip number to the selected semiconductor chip;

producing a lattice to divide a region in the selected semiconductor chip to which the chip number is assigned into rectangular regions the number of which exceeds the number of regions of at least two rows and two columns, on the basis of in-chip coordinates, selecting at least four lattice points from the lattice points of the lattice, selecting a pattern in the vicinity of the selected lattice points from the pattern formed on the wafer as only one candidate measurement point with respect to the lattice points, and assigning a candidate measurement point number to the candidate measurement point; and defining only some of the candidate measurement points to which the candidate measurement point numbers have been assigned as first measurement points to be actually measured based on a fractional factorial design for each of the respective semiconductor chips to which the chip numbers have been assigned.

According to a sixth aspect of the present invention, there is provided a program which allows a computer to implement a pattern inspection method, said pattern inspection method comprising:

assigning first wafer numbers in order of a process to a wafer group constituted of a plurality of wafers including a semiconductor chip group respectively, the semiconductor chip group having a plurality of chips, each semiconductor chip having a pattern formed thereon in the process;

dividing the wafer group into at least two first sub-groups in accordance with the first wafer numbers, and selecting at least two wafers having serial first wafer numbers from the first sub-groups to assign second wafer numbers to the selected wafers, respectively;

dividing the semiconductor chip group into at least two second sub-groups in accordance with distances between center positions of semiconductor chips on the wafers to which the second wafer numbers have been assigned and center positions of the wafers, selecting at least three semiconductor chips from the second sub-groups, further selecting a chip including the center position of the wafer inside thereof if any, and assigning a chip number to the selected semiconductor chip;

producing a lattice to divide a region in the selected semiconductor chip to which the chip number is assigned into rectangular regions the number of which exceeds the number of regions of at least two rows and two columns, on the basis of in-chip coordinates, selecting at least four lattice points from the lattice points of the lattice, selecting a pattern in the vicinity of the selected lattice points from the pattern formed on the wafer as only one candidate measurement point with respect to the lattice points, and assigning a candidate measurement point number to the candidate measurement point;

defining only some of the candidate measurement points to which the candidate measurement point numbers have been assigned as first measurement points to be actually measured based on a fractional factorial design for each of the respective semiconductor chips to which the chip numbers have been assigned;

preparing a measurement schedule and actually executing measurement to the defined measurement points;

executing an analysis of variance from obtained measurement results on the basis of the fractional factorial design; and changing the measurement schedule on the basis of the result of the analysis of variance.

According to a seventh aspect of the present invention, there is provided a pattern inspection apparatus which is capable to communicate with an external inspection device and which prepares a schedule to measure a pattern to supply the prepared measurement schedule to the external inspection device, said pattern inspection apparatus comprising:

a controller which receives information of a measurement point defined as a point to be actually measured to prepare a measurement schedule and supplies a first command signal to execute measurement to the defined measurement point to the external inspection device, the measurement point being defined by:

assigning first wafer numbers in order of a process with respect to a wafer group constituted of a plurality of wafers including semiconductor chip groups in which patterns are formed by a fine processing process;

dividing the wafer group into at least two first sub-groups in accordance with the first wafer numbers, and selecting at least two or more wafers having serial first wafer numbers from the first sub-group to assign second wafer numbers;

dividing the semiconductor chip group into at least two second sub-groups in accordance with distances between center positions of semiconductor chips on the wafers to which the second wafer numbers have been assigned and center positions of the wafers, selecting at least three semiconductor chips from the second sub-group, further selecting a chip including the center position of the wafer inside if any, and assigning a chip number to the selected semiconductor chip;

producing a lattice to divide a region in the selected semiconductor chip to which the chip number is assigned into rectangular regions exceeding a quantity of at least two rows and two columns based on in-chip coordinates, selecting at least four lattice points from the lattice points of the lattice, selecting a pattern in the vicinity of the selected lattice points in the pattern formed on the wafer as only one candidate measurement point with respect to the lattice point, and assigning a candidate measurement point number to the candidate measurement point; and selecting only some of the candidate measurement points to which the candidate measurement point numbers have been assigned based on a fractional factorial design with respect to the respective semiconductor chips to which the chip numbers have been assigned.

BRIEF DESCRIPTION OF THE DRAWINGS

FIG. 9 is a diagram showing one example of an orthogonal array;

DETAILED DESCRIPTION OF THE INVENTION

Some embodiments of the present invention will hereinafter be described with reference to the drawings.

FIRST EMBODIMENT

A first embodiment of the present invention will be described with reference to FIGS. 1 to 7. A method of selecting a pattern to be measured with respect to a wafer group constituted of n (n≧4) wafers subjected to a lithography process will hereinafter be described. The present embodiment will be explained with an example of the wafer group constituted of n=24 wafers.

Figure 1:
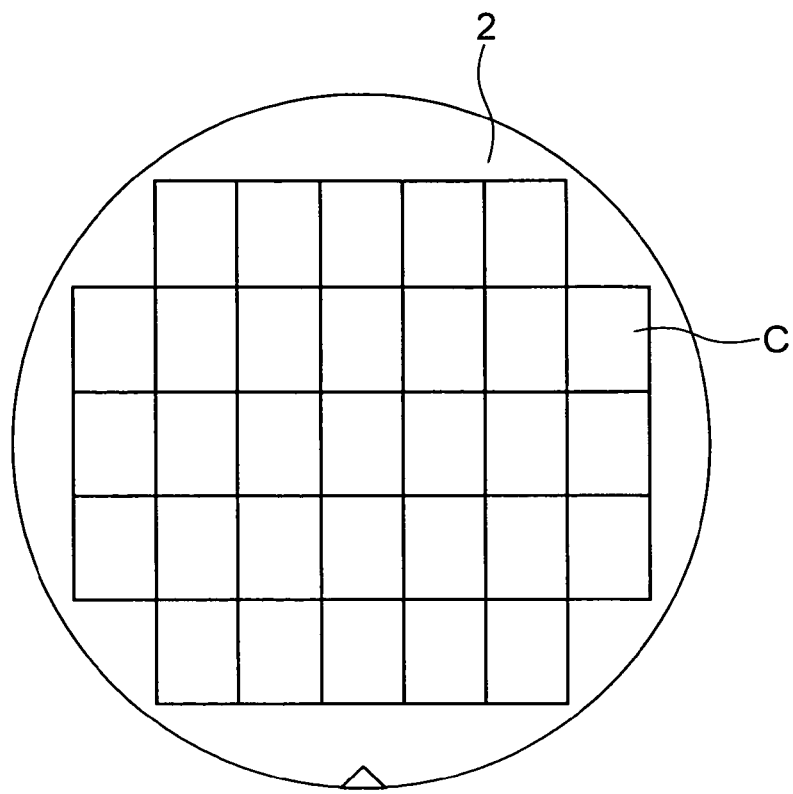
FIG. 1 is a schematic diagram showing a wafer constituting a wafer group to be measured in a first embodiment of the present invention.
Figure 2:
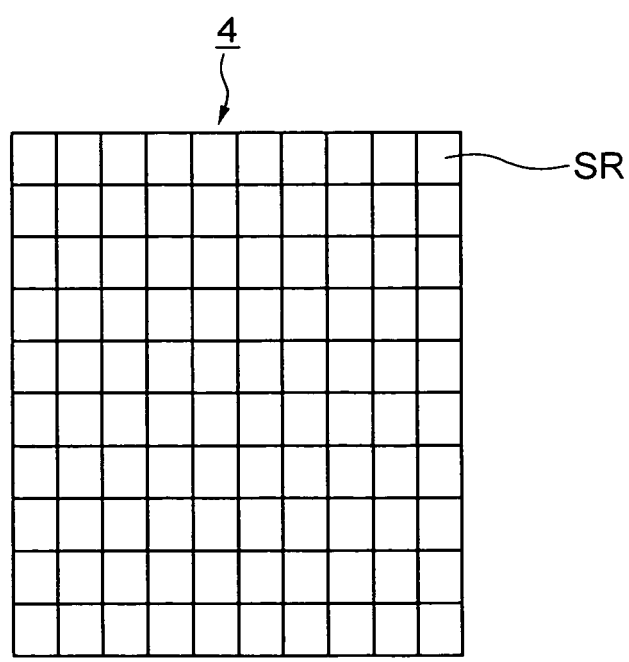
FIG. 2 is a schematic diagram showing a photo mask for use in forming the wafer shown in FIG. 1.

FIG. 1 is a schematic diagram of a wafer 2 constituting the wafer group to be measured. As shown in the figure, semiconductor chips C are arranged in the wafer 2. Each chip C is formed using a photo mask 4 shown in FIG. 2. In this photo mask 4, an equivalent pattern is disposed for each of 10 rows×10 columns sub-regions SR.

Figure 3:
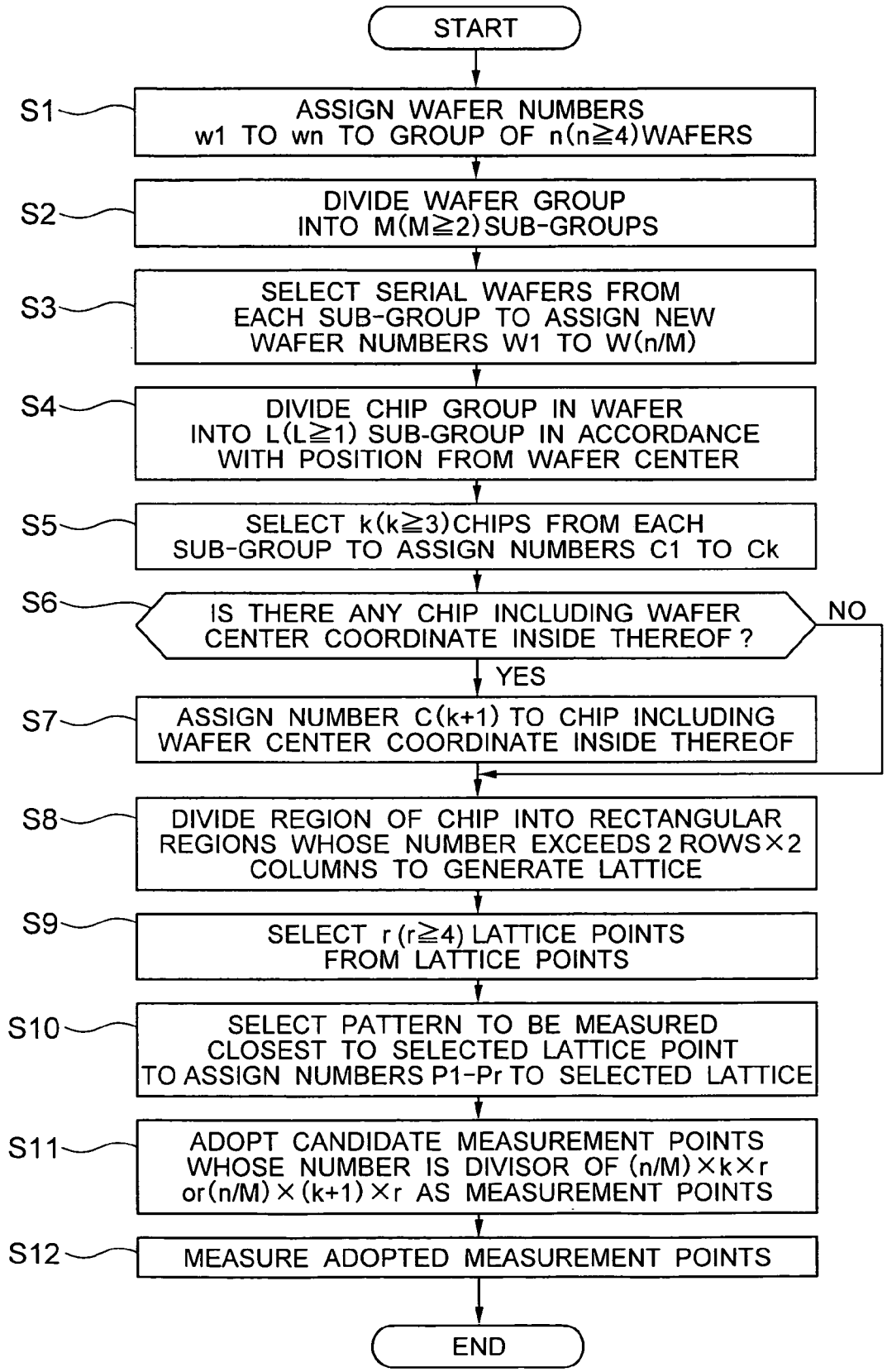
FIG. 3 is a flowchart showing a schematic procedure of the first embodiment of the present invention.

FIG. 3 is a flowchart including a schematic procedure of a method of selecting a pattern to be measured in the present embodiment.

As shown in the figure, first, wafer numbers w1, w2 . . . and w24 are successively assigned to 24 wafers in order of the wafers successively processed by a lithography process (step S1).

Next, a wafer group of 24 wafers is divided into M (M≧2) sub-groups by the wafer number (step S2). In the present embodiment, the wafers are grouped in such a manner that a first group is constituted of wafers having wafer numbers w1 to w8, a second group is constituted of wafers having wafer numbers w9 to w16, and further a third group is constituted of wafers having wafer numbers w17 to w24 (M=3).

Next, serial wafers are selected from each sub-group, and new wafer numbers are assigned (step S3). Specifically, wafers w1, w2, w3 were selected from the first sub-group to assign new wafer numbers W1, W2, W3, respectively. Similarly, wafers w12, w13 were selected from a second sub-group to assign new wafer numbers W4, W5, and further wafers w22, w23, w24 were selected from a third sub-group to assign new wafer numbers W6, W7, W8.

Figure 4:
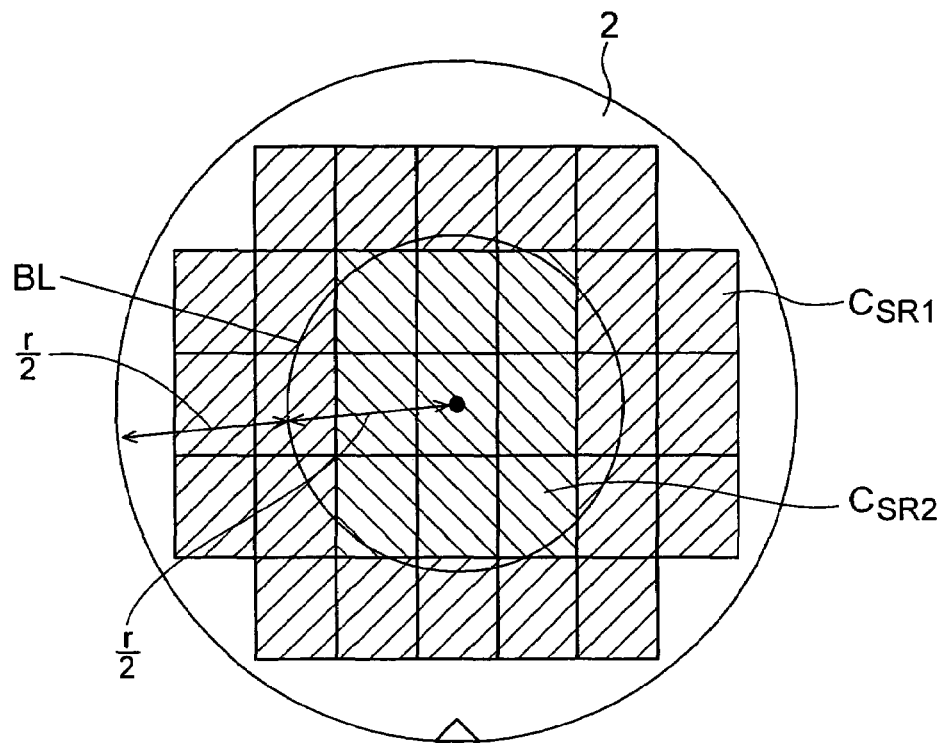
FIGS. 4 to 6C are explanatory views of the procedure shown in the flowchart of FIG. 3.

Next, a chip group in the wafer is divided into two (L=2) sub-groups in accordance with a distance from a center of the wafer (step S4). Specifically, as shown in FIG. 4, assuming that a radius of the wafer 2 is r, a boundary line BL of a virtual circular shape having a radius ½r in the wafer 2 and including a wafer center coordinate as an origin is defined. The chip group was divided into sub-groups CSR1 and CSR2, the sub-group CSR1 being constituted of the chips whose chip center coordinate was outside the boundary line BL, and the sub-group CSR2 being constituted of the chips whose coordinate was inside the line.

Figure 5:
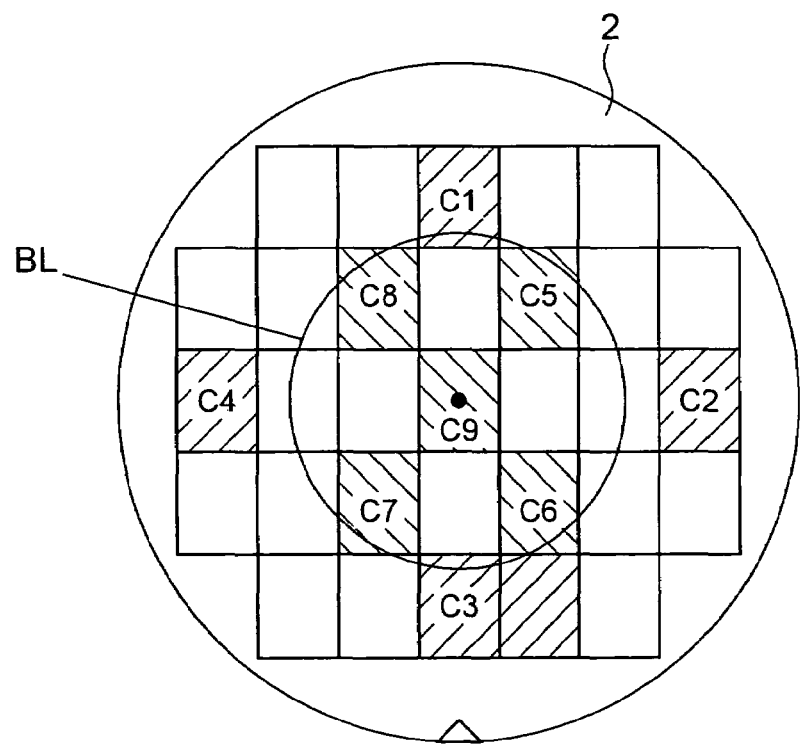

Next, k (k≧3) chips are selected from each sub-group to assign chip numbers C1 to Ck to these chips (step S5). In the present embodiment, as shown in FIG. 5, the chips were selected for every k=4 chips, and chip numbers C1 to C8 were assigned. Furthermore, when there is the chip including the wafer center coordinate inside thereof (step S6), chip number C(k+1) is assigned to this chip (step S7). In the present embodiment, chip number 9 was assigned.

Figure 6A:
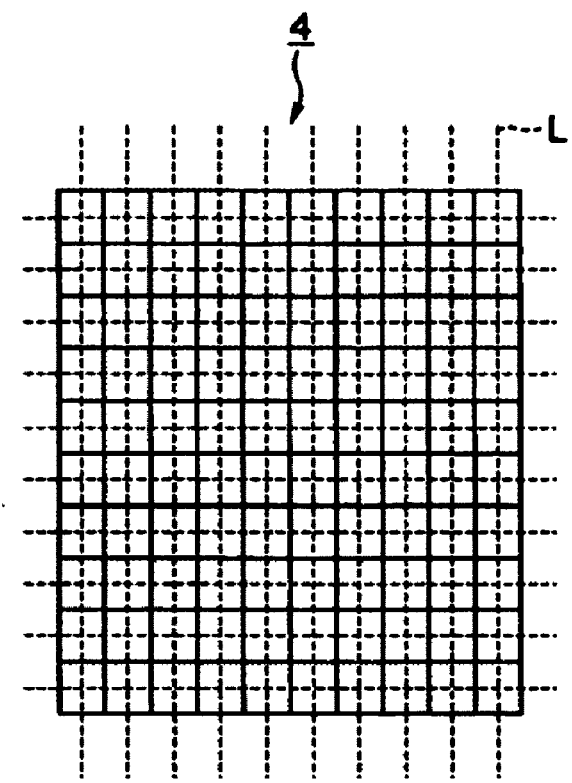

Next, the region of the chip is divided into rectangular regions the number of which exceeds 2 (rows)×2 (columns) to form a lattice using center points of an equivalent sub-chips included in the chip (step S8). In the present embodiment, the region of the chip was divided into regions of 10 rows×10 columns as shown in FIG. 6A.

Figure 6B:
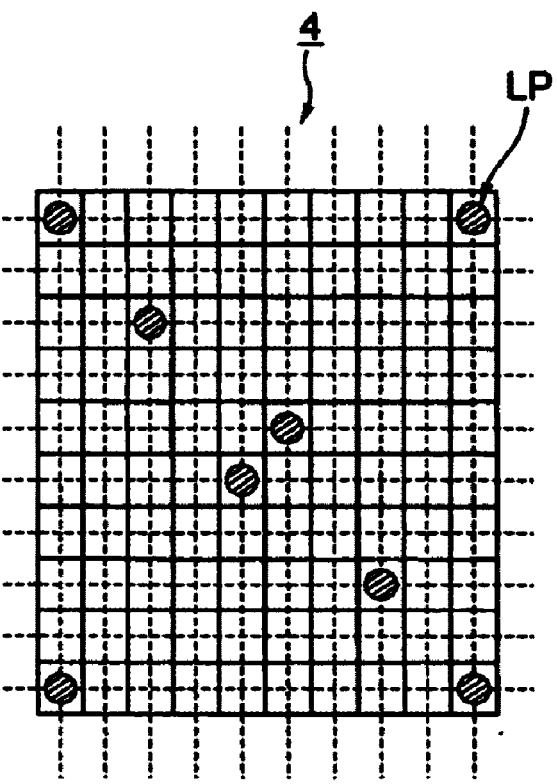

Next, r (r≧4) lattice points are selected from lattice points obtained by dividing the lattice (step S9). In the present embodiment, as shown in FIG. 6B, eight lattice points were selected.

Figure 6C:
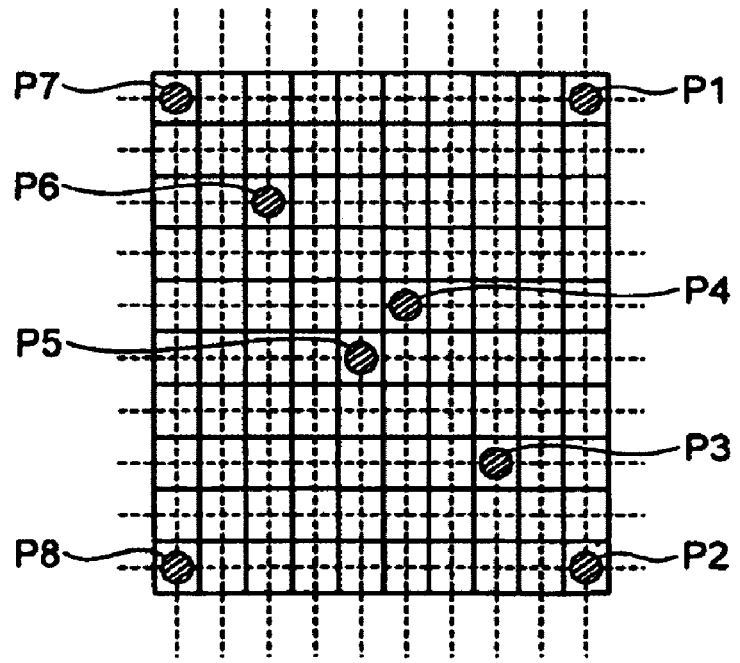

Next, the pattern to be measured closest to the selected lattice point is selected, and pattern numbers P1 to Pr are assigned (step S10). In the present embodiment, as shown in FIG. 6C, numbers P1 to P8 were assigned.

The quantity of candidate measurement points selected by the above-described steps S1 to S10 is (n/M)×(k+1)×r. The quantity was 8×9×8=576 points in the present embodiment.

Next, from (n/M)×(k+1)×r candidate measurement points, candidate measurement point, the number of which corresponds to a divisor of (n/M)×(k+1)×r, is selected and the selected candidate measurement points is adopted as a measurement point to be actually measured (step S11). In the present embodiment, from 576 candidate measurement points, only candidate measurement points P1, P3, P5, P7 were adopted as the measurement points to be actually measured with respect to wafer numbers W1, W3, W5, W7, and only candidate measurement points P2, P4, P6, P8 were adopted as the measurement points with respect to wafer numbers W2, W4, W6, W8. As a result, the number of measurement points was 288 points.

Such design of experiment method in which only points are selected from a combination of all factors (i.e., fluctuation between the wafers: degree of freedom of 7, the fluctuation in the wafer: the degree of freedom of 8, the fluctuation in the chip: degree of freedom of 7) and the selected points are actually measured the number of which corresponds to a divisor of the combination of all the factors is called a fractional factorial design as taught by statistics. In the present embodiment, since this method is used, major effects of the factors can be checked without checking all the combinations, and therefore a measurement cost can be reduced.

Finally, the adopted 288 measurement points were actually measured (step S12).

As a result of selection of the measurement pattern by the above-described procedure, it was possible to set the total number of measurement points to 288 points although the degrees of freedom were 7, 8, 7 with respect to the dimensional fluctuations between the wafers, between the chips, and in the chip, respectively. In accordance with a conventional method, the total number is usually (7+1)×(8+1)×(7+1)=576. Therefore, it was possible to reduce the number of measurement points to ½ of a conventional number.

In accordance with the present embodiment, an estimation precision of statistic in a pattern dimension or alignment deviation in one lot is thus largely enhanced.

It is to be noted that the respective steps of the flowchart shown in FIG. 3 were executed in a numerical order in the present embodiment, but the method of selecting a pattern to be measured according to the present invention does not have to be necessarily carried out in the same order as that of the procedure shown in FIG. 3.

In the present embodiment, ½ of all the combinations were selected for the fractional replication, but this does not limit the scope of the present invention, and the arbitrary divisor number of combinations such as ¼, ⅛ can be selected in accordance with the cost of measurement.

Moreover, in the present embodiment, in order to enhance the estimation precision of the fluctuation of the pattern dimension and alignment deviation without increasing the cost of measurement, the numbers of wafers, chips, and patterns in the chip, which were measurement candidates, were set to 8, 9, 8, respectively. These numbers do not limit the scope of the present invention, but in order to secure the precision during calculation of the fluctuation of each factor, the respective numbers are preferably set to 8 or more. Further for a purpose of preventing the measurement cost from increasing, the numbers are preferably about 8 to 9, respectively.

For a purpose of further reducing the cost of measurement, some of the measurement points defined by the above-described method may further be selected and measured.

SECOND EMBODIMENT

Next, a second embodiment of the present invention will be described with reference to FIGS. 7 to 11. The present embodiment also provides the method of selecting a pattern to be measured, and characteristics thereof lie in that an orthogonal array is used to further limit and select the candidate measurement points.

Figure 7:
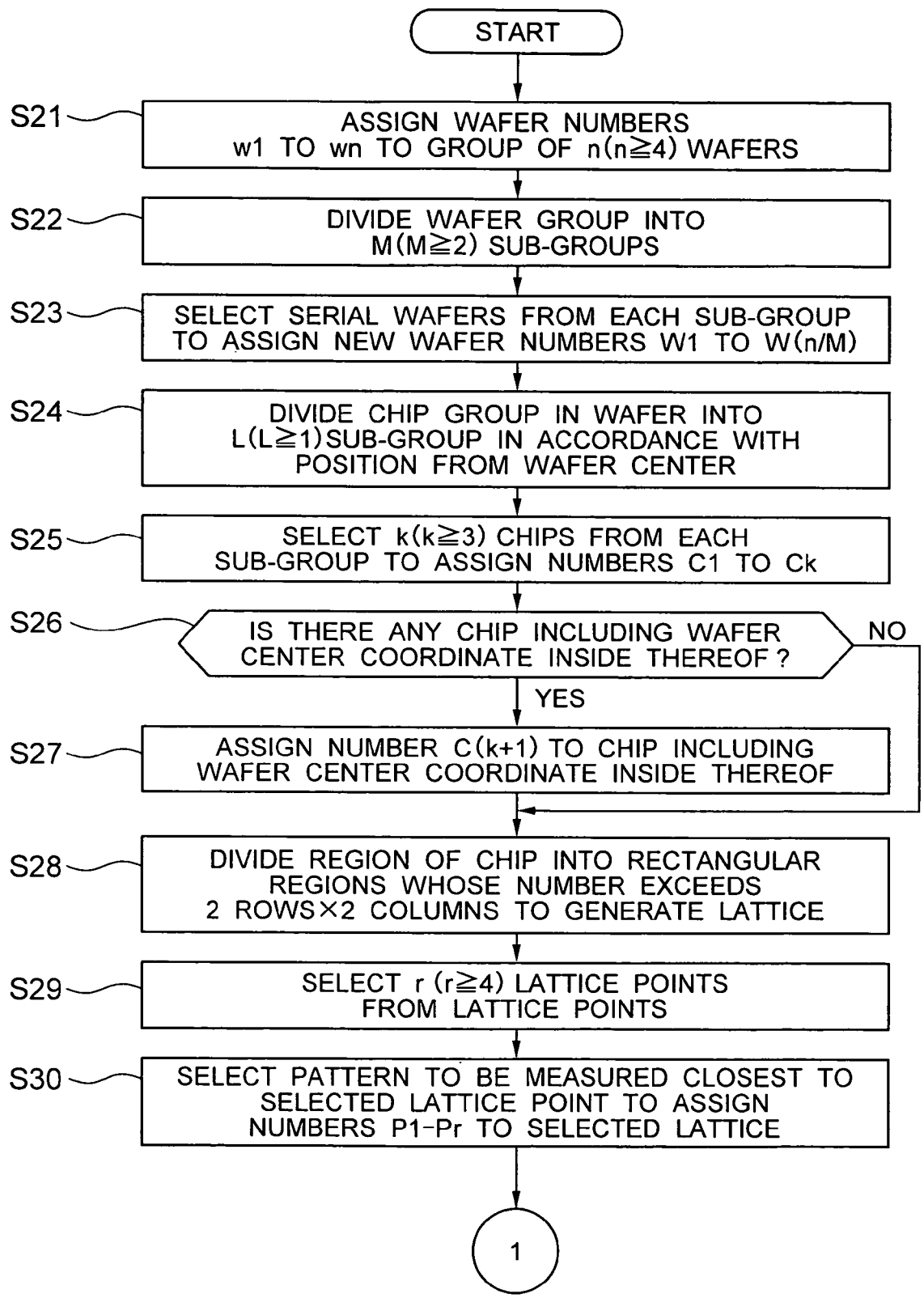
FIGS. 7 and 8 are flowcharts showing schematic procedures of a second embodiment of the present invention.
Figure 8:
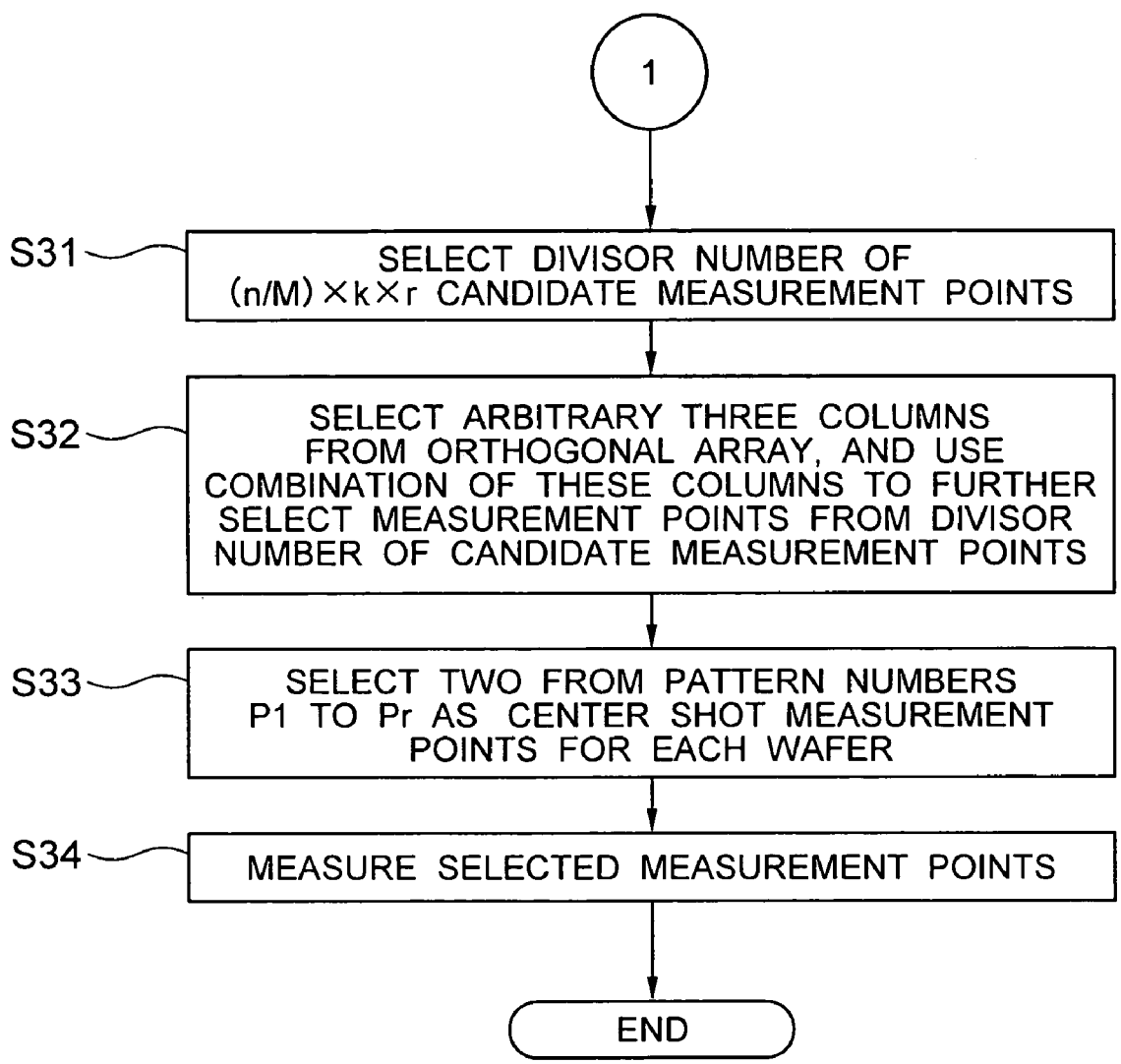

FIGS. 7 and 8 are flowcharts showing schematic procedures of the method of selecting a pattern to be measured according to the present embodiment. Steps S21 to S30 shown in FIG. 7 are substantially the same as the steps S11 to S20 shown in FIG. 3, and are equivalent to steps having step numbers to each of which 10 is added. Therefore, the procedure shown in FIG. 8 will hereinafter be described.

After selecting the number corresponding to the divisor number of candidate measurement points (n/M)×k×r candidate measurement points excluding a center chip (step S31), arbitrary three columns are selected from the orthogonal array, and a combination of these columns are used to further select the measurement points from the divisor number of the candidate measurement points excluding the center chip (step S32).

Figure 9:
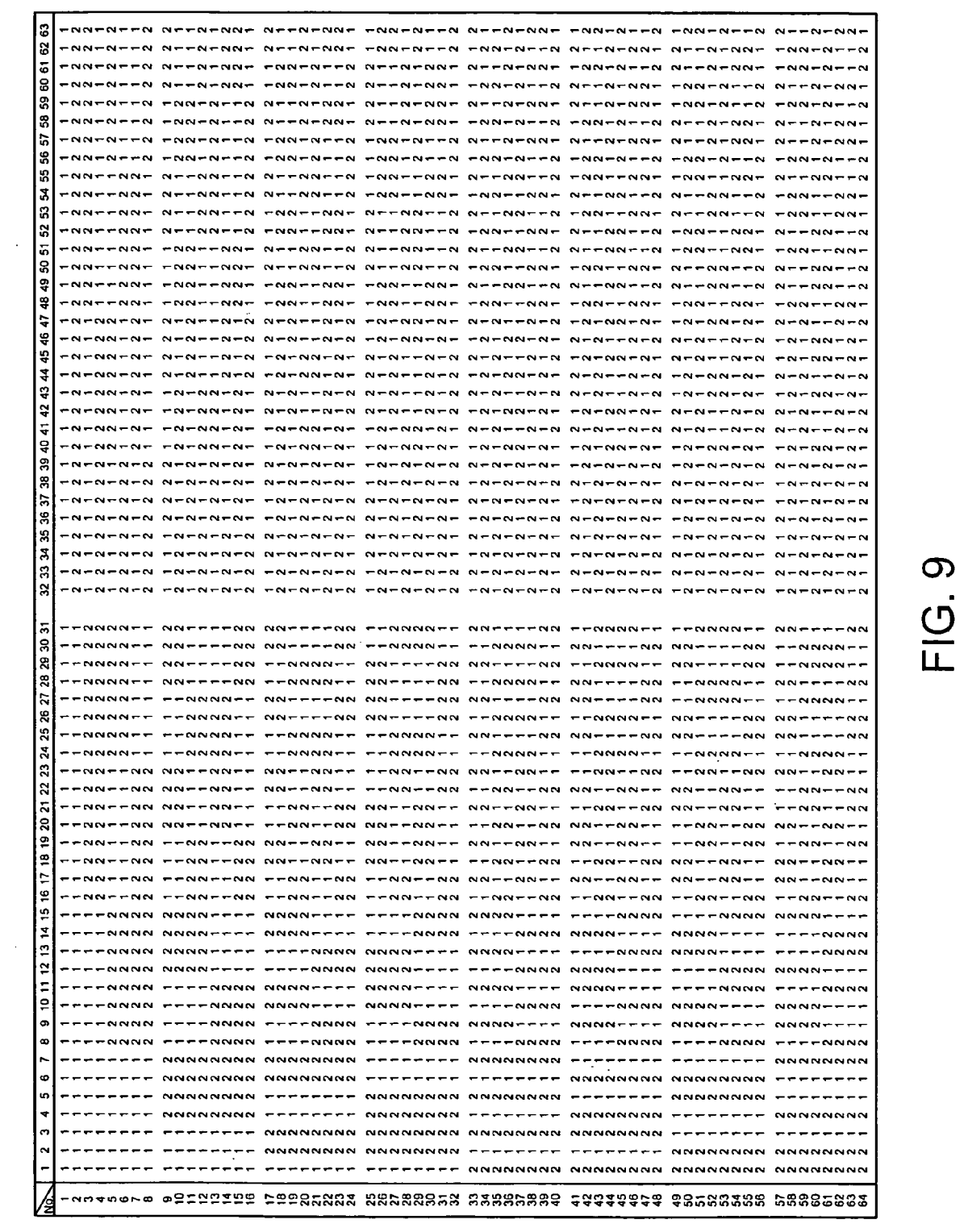

FIG. 9 shows one example of the orthogonal array. An L64 orthogonal array shown in this figure is an orthogonal array for allocating two levels and 63 factors as described in, for example, pp. 1058 to 1070 of "Design of Experiment Method, vol. 2" authored by Genichi Taguchi, Maruzen Co., Ltd., 1977. It is possible to select arbitrary three columns from this L64 orthogonal array and to newly allocate the factors of eight levels by the combination of the three columns. In the present embodiment, the eight level factors newly prepared by a combination of eighth, 16th, and 23rd columns were associated with the wafer numbers W1 to W8, the eight level factors newly prepared by a combination of first, second, and fourth columns were associated with the chip numbers C1 to C8, and the eight level factors newly prepared by a combination of 27th, 32nd, and 45th columns were associated with the pattern numbers P1 to P8. As a result, 64 points were selected from 512 candidate measurement points, for example, in W1, like P1 and P4 in C1, P6 and P7 in C4, and so forth.

Furthermore, two points are selected as center shot measurement points from P1 to P8 for each wafer (step S33) and the selected measurement points are actually measured.

Figure 10:
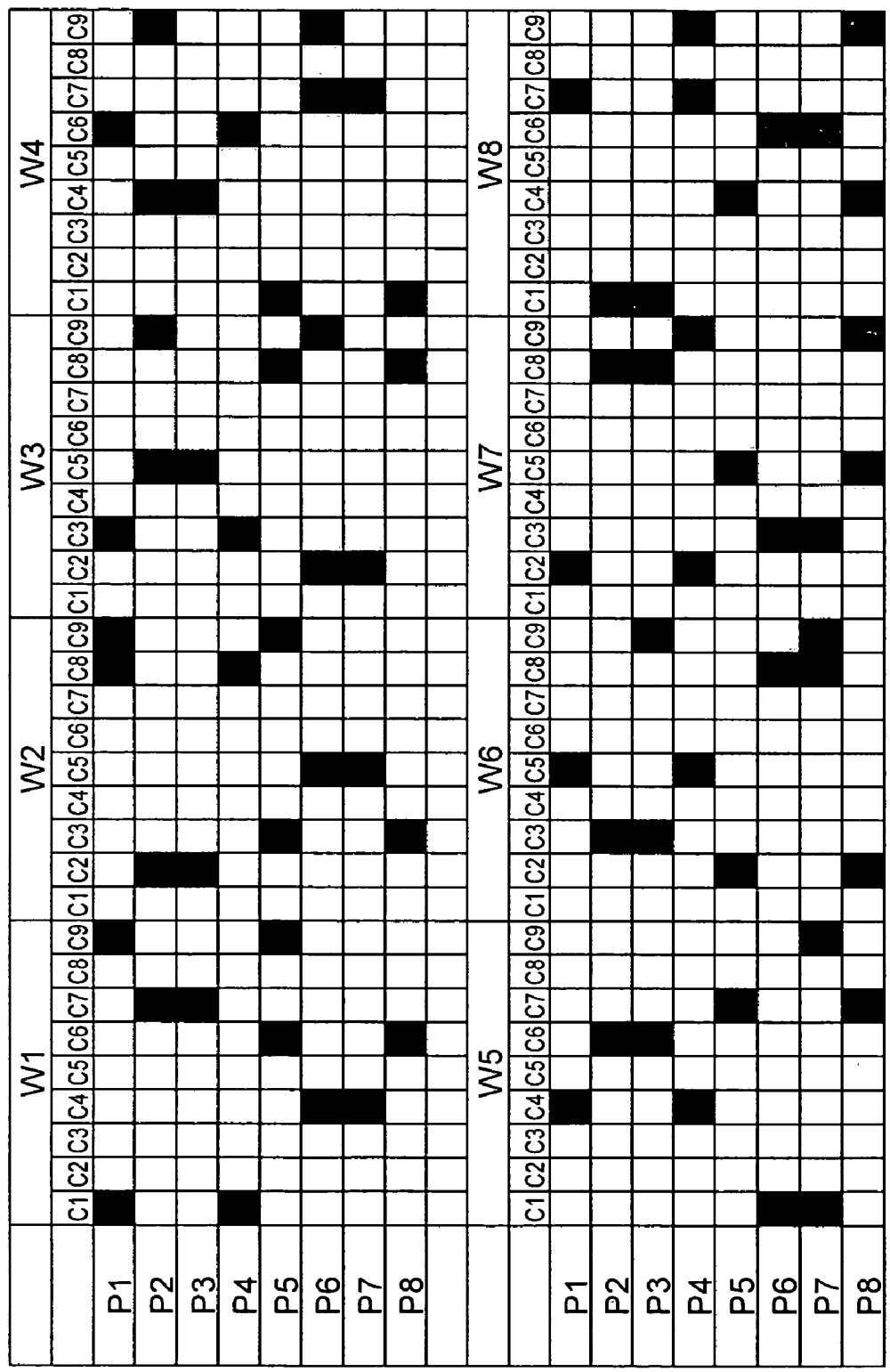
FIG. 10 is a diagram showing an example of a measurement point defined based on the orthogonal array shown in FIG. 9.

By the above-described procedure, 80 measurement points were defined as shown in solid black portions of FIG. 10.

As a result, it is possible to set the number of measurement points in one lot to 80 points while the degrees of freedom are kept as 7, 8, 7 with respect to the dimensional fluctuations between the wafers, between the chips, and in the chip. Additionally, it is possible to implement the measurement without any deviation of alternate functions among the factors.

Also in the present embodiment, in order to further reduce the cost of measurement, further some points may be selected from the measurement points defined by the above-described procedure to execute the measurement.

THIRD EMBODIMENT

A third embodiment provides a method of preparing a schedule to measure a semiconductor pattern.

In accordance with the second embodiment, the number of the wafer to be actually measured in the wafer group, and the measurement shot in each wafer and the position in the shot were determined. Measurement point information obtained as this result is inserted, for example, into the corresponding data position in a recipe file of a CD-SEM.

This has heretofore depended on a level of skill of an engineer, and therefore there have been many errors in the prepared measurement schedule.

In accordance with the present embodiment, since the measurement schedule is prepared based on the above-described factorial design, it is possible to automatically prepare a schedule without any error. Accordingly, it is possible to easily and quickly prepare, for example, measurement recipes of a length measurement device and alignment deviation inspection device.

FOURTH EMBODIMENT

The present embodiment provides an inspection method of a semiconductor pattern. The characteristics of the inspection method of the pattern in the present embodiment lie in that the measurement is actually executed in accordance with the measurement schedule prepared by the second embodiment, contribution ratios of fluctuation factors are judged from the measurement result, and this judgment result is used to further limit the number of measurement points.

Figure 11:
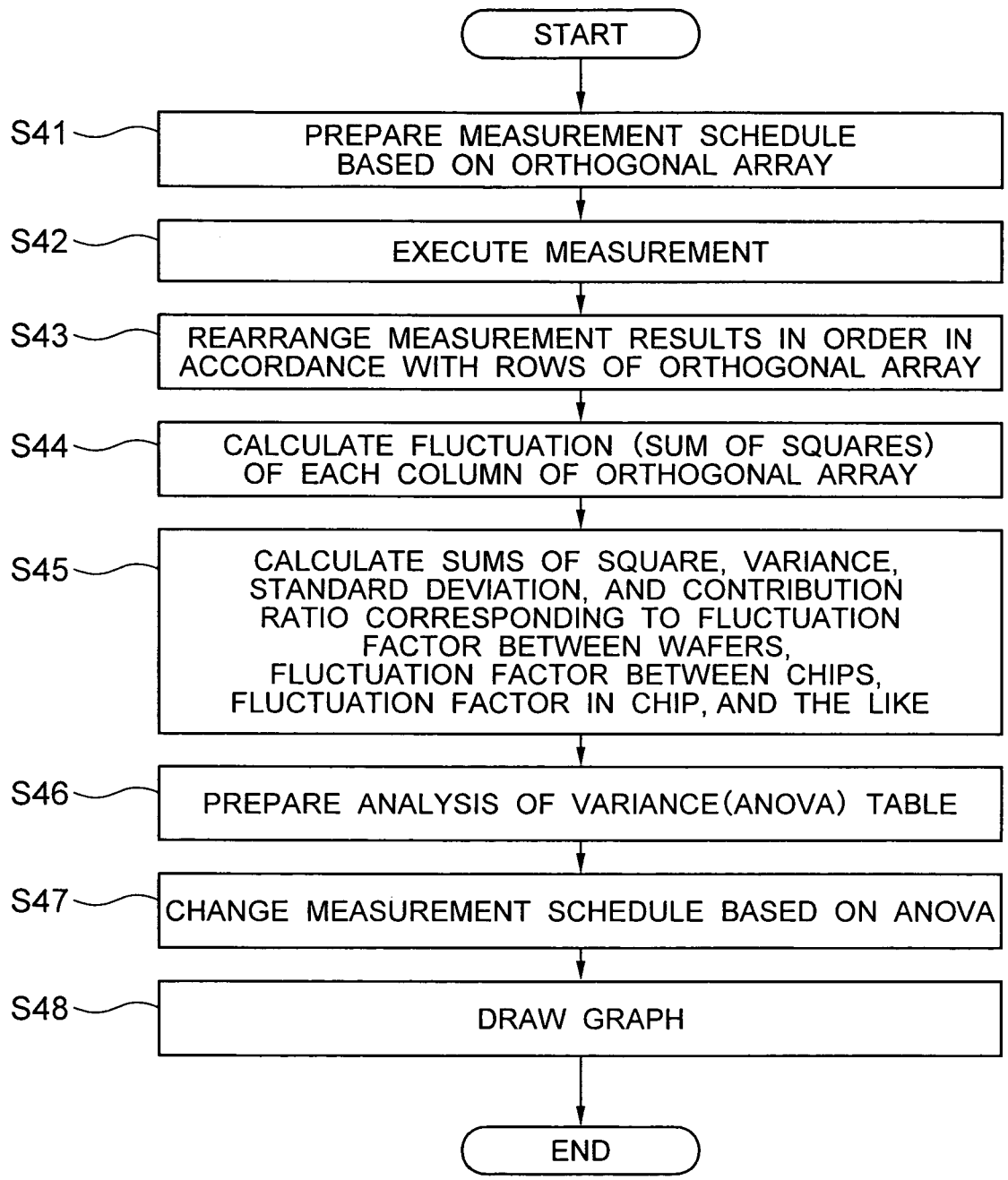
FIG. 11 is a flowchart showing the schematic procedure of a fourth embodiment of the present invention.

FIG. 11 is a flowchart showing the schematic procedure of the pattern inspection method of the present embodiment.

First, the measurement schedule is prepared by the procedure shown in FIGS. 7 and 8 (step S41), and the measurement is actually executed (step S42).

Next, obtained measurement results are rearranged in order corresponding to the orthogonal array, the row of L64 orthogonal array in the present embodiment (step S43).

Next, a sum of squares corresponding to each column of the L64 orthogonal array is calculated (step S44).

Subsequently, the sum of squares, variance, standard deviation, contribution ratio are calculated corresponding to fluctuation components between the wafers, between the chips, and in the chip, and other error factors in accordance with the combination of columns of the L64 orthogonal array corresponding to the wafer number, chip number, and measurement point number (step S45), and an analysis of variance (ANOVA) table is prepared (step S46).

Next, the measurement schedule is changed based on the prepared ANOVA (step S47). For example, when the contribution ratio of the fluctuation between the wafers is turned out to be small as a result of the preparation of ANOVA, the number of wafers to be measured is changed to four from eight, 80 measurement points are changed to 40 points by the fractional factorial design, and thereafter 40 points are measured with respect to the lot processed by the same process. It is to be noted that a dummy method may be used to omit the fluctuation component between the wafers.

Finally, a graph is drawn based on magnitudes of major effects and alternate functions obtained as a result of the analysis of variance (step S48). Furthermore, after calculating average values with respect to the chip numbers C1 to C9, the average values are represented as a function of an in-wafer coordinate, and further the result of approximation of this function to a quadric surface is represented in contour. Accordingly, it is possible to more easily analyze the fluctuation components between the chips.

In accordance with the present embodiment, it is thus possible to easily analyze the fluctuation factors of the pattern dimension and alignment deviation from the actual measurement result.

FIFTH EMBODIMENT

The present embodiment provides an inspection method of a semiconductor pattern, in which a measurement fluctuation is small. The characteristics of the present embodiment lie in that a dimension measurement result with respect to a calibration wafer constituting a standard for a measured value is used to judge precision of measurement in accordance with the measurement schedule obtained by the second embodiment prior to actual measurement.

First, the calibration wafer constituting the standard for the measured value is used to repeatedly measure the dimension of the same portion 20 times, and a ratio of a value obtained by multiplying a standard deviation σ by 5.15 to a dimensional tolerance is obtained.

Next, a dimensional precision of measurement by the above-described measurement schedule is estimated from the ratio of obtained 5.15 σ to the dimensional tolerance. For example, when the ratio of 5.15 σ to the dimensional tolerance is 42%, it is found that there is no precision in the dimension obtained by the measurement in accordance with the measurement schedule prepared in the second embodiment.

To solve the problem, the measurement is repeated twice in accordance with to the measurement schedule prepared based on the L64 orthogonal array, and the average value of two measurements is adopted as the measurement value. Accordingly, the same effect as that in substantially reducing the measurement fluctuation to 30% from 42% is obtained, and the cost of measurement can be reduced.

SIXTH EMBODIMENT

A sixth embodiment provides a pattern inspection apparatus which implements the method of selecting a pattern to be measured and the pattern inspection method.

Figure 12:
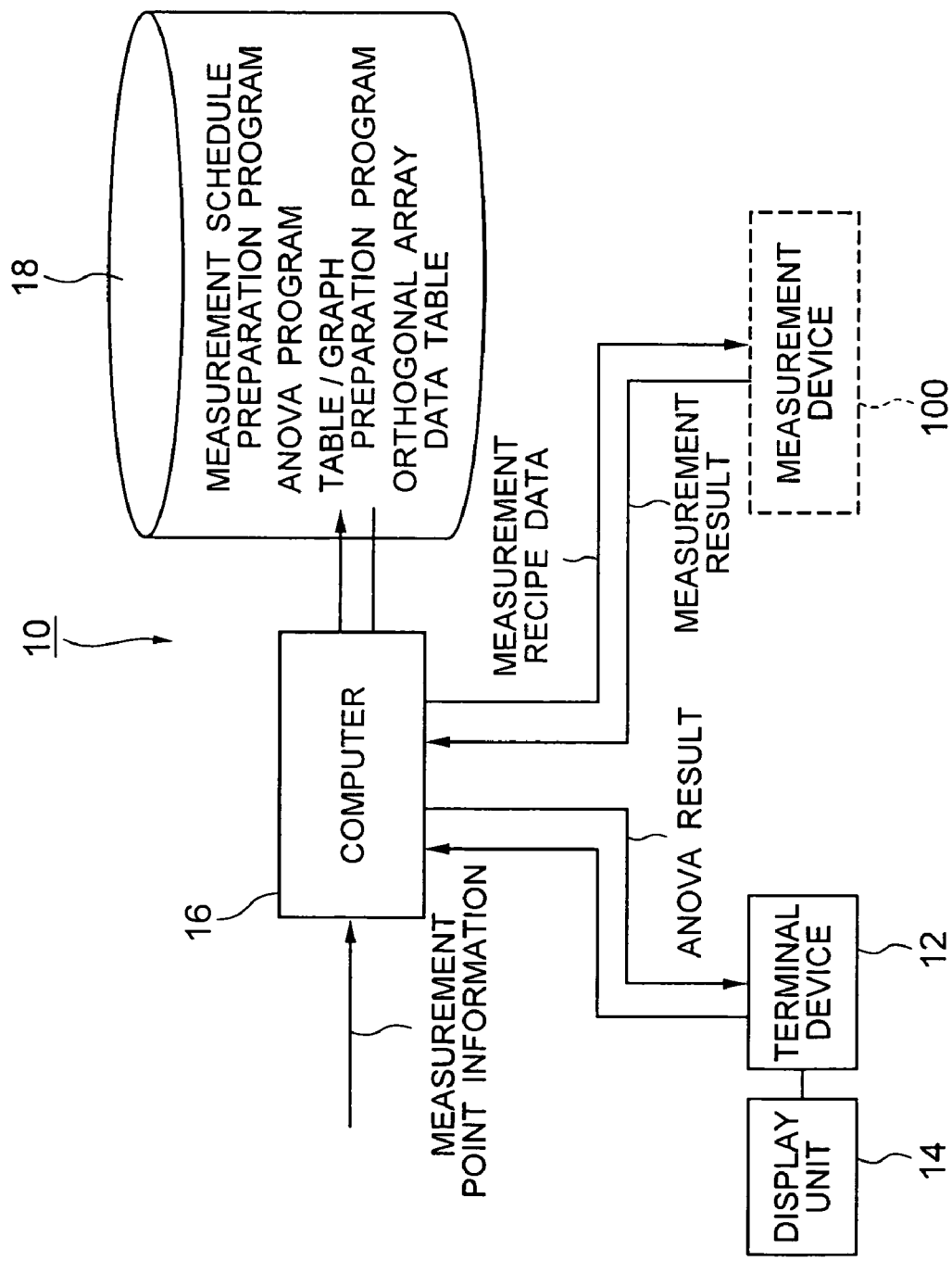
FIG. 12 is a block diagram showing the schematic constitution of a pattern inspection apparatus according to a sixth embodiment of the present invention.

FIG. 12 is a block diagram showing the schematic constitution of the pattern inspection apparatus of the present embodiment. A pattern inspection apparatus 10 shown in the figure comprises a computer 16, recording equipment 18 such as a hard disk drive connected to the computer 16, a terminal device 12 connected to the computer 16, and a display unit 14 connected to the terminal device 12.

The recording equipment 18 stores recipe files of a measurement schedule preparation program, ANOVA program, table/graph preparation program and a data table of the orthogonal array.

The computer 16 receives the measurement point information, reads the measurement schedule preparation program from the recording equipment 18 and prepares the measurement schedule by selecting the pattern to be measured with reference to the data table of the orthogonal array.

The computer 16 is connected to an external measurement device 100, and supplies the prepared measurement schedule as measurement recipe data to the measurement device 100. The measurement device 100 inserts the measurement recipe data into the corresponding data position of the recipe file (not shown), actually executes the measurement to the wafer group, and feeds back the measurement result to the computer 16. The computer 16 extracts the ANOVA program and table/graph preparation program from the recording equipment 18, and executes the ANOVA described in the fourth embodiment based on the measurement result sent from the measurement device 100 to prepare a table and graph on the basis of the obtained ANOVA. The ANOVA result and the table/graph are supplied to the terminal device 12 and displayed by the display unit 14.

The computer 16 can also change the measurement schedule in accordance with the procedure by the above-described fourth embodiment. In this case, the changed measurement schedule is supplied as new measurement recipe data to the measurement device 100.

The computer 16 can also judge the dimensional precision of the measurement implemented by the prepared measurement schedule in accordance with the fifth embodiment prior to the actual measurement. In this case, when the estimated dimensional precision is low, the measurement device 100 executes the measurement twice in accordance with the measurement schedule based on the orthogonal array, and the computer 16 calculates the average value of the sent results of two measurements, and displays this value as the measurement value in the display unit 14 via the terminal device 12.

In accordance with the present embodiment, the cost of measurement is thus reduced, and the fluctuation factor can easily be diagnosed. Therefore, it is possible to execute pattern inspection with high estimation precision of statistic by a simple arrangement, for example, in the pattern dimension and alignment deviation with respect to the wafers in one lot.

(7) Program and Recording Medium

A series of procedure of the method of selecting a pattern to be measured or the pattern inspection method may also be incorporated in the program and read and executed by a computer. Accordingly, the method of selecting a pattern to be measured or the pattern inspection method according to the present invention can be realized using a general-purpose computer. Moreover, the series of procedure of the method of selecting a pattern to be measured or the pattern inspection method may also be stored as a program to be executed by a computer in a recording medium such as a flexible disk and CD-ROM, and read and executed by the computer.

The recording media are not limited to portable media such as a magnetic disk and optical disk, and may also be fixed recording media such as a hard disk drive and memory. The program in which the series of procedure of the method of selecting a pattern to be measured or the pattern inspection method is incorporated may also be distributed via communication circuits such as internet (including radio communication). Furthermore, the program in which series of procedure of the method of selecting a pattern to be measured or the pattern inspection method is incorporated may be encrypted, modified, or compressed. In this state, the program may also be stored in the recording media and distributed via wires such as internet or via radio.

(8) Method of Manufacturing Semiconductor Device

When a semiconductor device is manufactured by a process including a low-cost/high-precision inspection process using the method of selecting a pattern to be measured or the pattern inspection method, the semiconductor device can be manufactured with high throughput and yield.

Several embodiments of the present invention have been described above, but the present invention is not limited to the above-described modes, and can, needless to say, be modified and carried out variously without departing from the scope thereof. In the above embodiment, a CD-SEM and an alignment deviation inspection apparatus are exemplified as specific examples of the inspection apparatus, but the present invention can also be applied, for example, to an optical apparatus called scatterometry.

What is claimed is:

1. A method of selecting a pattern to be measured comprising:
    assigning first wafer numbers in order of a process to a wafer group constituted of a plurality of wafers including a semiconductor chip group respectively, the semiconductor chip group having a plurality of chips, each semiconductor chip having a pattern formed thereon in the process;
    dividing the wafer group into at least two first sub-groups in accordance with the first wafer numbers, and selecting at least two wafers having serial first wafer numbers from the first sub-groups to assign second wafer numbers to the selected wafers, respectively;
    dividing the semiconductor chip group into at least two second sub-groups in accordance with distances between center positions of semiconductor chips on the wafers to which the second wafer numbers have been assigned and center positions of the wafers, selecting at least three semiconductor chips from the second sub-groups, further selecting a chip including the center position of the wafer inside thereof if any, and assigning a chip number to the selected semiconductor chip;
    producing a lattice to divide a region in the selected semiconductor chip to which the chip number is assigned into rectangular regions the number of which exceeds the number of regions of at least two rows and two columns, on the basis of in-chip coordinates, selecting at least four lattice points from the lattice points of the lattice, selecting a pattern in the vicinity of the selected lattice points from the pattern formed on the wafer as only one candidate measurement point with respect to the lattice points, and assigning a candidate measurement point number to the candidate measurement point; and
    defining only some of the candidate measurement points to which the candidate measurement point numbers have been assigned as first measurement points to be actually measured based on a fractional factorial design for each of the respective semiconductor chips to which the chip numbers have been assigned.

2. The method of selecting a pattern to be measured according to claim 1,
    wherein the fractional factorial design includes experimental arrangement based on an orthogonal array method.

3. The method of selecting a pattern to be measured according to claim 2,
    wherein the orthogonal array method includes an orthogonal array method based on an L64 orthogonal array.

4. The method of selecting a pattern to be measured according to claim 1, further comprising:
    defining second measurement points by further selecting some of the first measurement points.

5. A pattern inspection method comprising:
    assigning first wafer numbers in order of a process to a wafer group constituted of a plurality of wafers including a semiconductor chip group respectively, the semiconductor chip group having a plurality of chips, each semiconductor chip having a pattern formed thereon in the process;
    dividing the wafer group into at least two first sub-groups in accordance with the first wafer numbers, and selecting at least two wafers having serial first wafer numbers from the first sub-groups to assign second wafer numbers to the selected wafers, respectively;
    dividing the semiconductor chip group into at least two second sub-groups in accordance with distances between center positions of semiconductor chips on the wafers to which the second wafer numbers have been assigned and center positions of the wafers, selecting at least three semiconductor chips from the second sub-groups, further selecting a chip including the center position of the wafer inside thereof if any, and assigning a chip number to the selected semiconductor chip;
    producing a lattice to divide a region in the selected semiconductor chip to which the chip number is assigned into rectangular regions the number of which exceeds the number of regions of at least two rows and two columns, on the basis of in-chip coordinates, selecting at least four lattice points from the lattice points of the lattice, selecting a pattern in the vicinity of the selected lattice points from the pattern formed on the wafer as only one candidate measurement point with respect to the lattice points, and assigning a candidate measurement point number to the candidate measurement point;
    defining only some of the candidate measurement points to which the candidate measurement point numbers have been assigned as first measurement points to be actually measured based on a fractional factorial design for each of the respective semiconductor chips to which the chip numbers have been assigned;
    preparing a measurement schedule and actually executing measurement to the defined measurement points;
    executing an analysis of variance from obtained measurement results on the basis of the fractional factorial design; and
    changing the measurement schedule on the basis of the result of the analysis of variance.

6. The pattern inspection method according to claim 5, further comprising: bringing the result of the analysis of variance into view in the form of a table or a graph.

7. The pattern inspection method according to claim 5, further comprising: omitting some of the defined measurement points to define new measurement points on the basis of the result of the analysis of variance.

8. The pattern inspection method according to claim 5,
    wherein said some of the defined measurement points are omitted in use of a dummy method.

9. A pattern inspection method using a measurement device, said method comprising:
    assigning first wafer numbers in order of a process to a wafer group constituted of a plurality of wafers including a semiconductor chip group respectively, the semiconductor chip group having a plurality of chips, each semiconductor chip having a pattern formed thereon in the process;

dividing the wafer group into at least two first sub-groups in accordance with the first wafer numbers, and selecting at least two wafers having serial first wafer numbers from the first sub-groups to assign second wafer numbers to the selected wafers, respectively;

dividing the semiconductor chip group into at least two second sub-groups in accordance with distances between center positions of semiconductor chips on the wafers to which the second wafer numbers have been assigned and center positions of the wafers, selecting at least three semiconductor chips from the second sub-groups, further selecting a chip including the center position of the wafer inside thereof if any, and assigning a chip number to the selected semiconductor chip;

producing a lattice to divide a region in the selected semiconductor chip to which the chip number is assigned into rectangular regions the number of which exceeds the number of regions of at least two rows and two columns, on the basis of in-chip coordinates, selecting at least four lattice points from the lattice points of the lattice, selecting a pattern in the vicinity of the selected lattice points from the pattern formed on the wafer as only one candidate measurement point with respect to the lattice points, and assigning a candidate measurement point number to the candidate measurement point;

defining only some of the candidate measurement points to which the candidate measurement point numbers have been assigned as first measurement points to be actually measured based on a fractional factorial design for each of the respective semiconductor chips to which the chip numbers have been assigned; and actually measuring a standard pattern prepared beforehand a predetermined times using the measurement device, prior to an actual measurement to the defined measurement point to evaluate reliability of the measurement device.

10. The pattern inspection method according to claim 9, further comprising: determining the number of measurements to the defined measurement points, when the result of evaluation of reliability of the measurement device is lower than a predetermined standard value, repeating the measurement to the measurement points by the determined number of measurements, and adopting an average value as a measured value of each measurement point.

11. A manufacturing method of a semiconductor device using a pattern inspection method, said pattern inspection method comprising:

assigning first wafer numbers in order of a process to a wafer group constituted of a plurality of wafers including a semiconductor chip group respectively, the semiconductor chip group having a plurality of chips, each semiconductor chip having a pattern formed thereon in the process;

dividing the wafer group into at least two first sub-groups in accordance with the first wafer numbers, and selecting at least two wafers having serial first wafer numbers from the first sub-groups to assign second wafer numbers to the selected wafers, respectively;

dividing the semiconductor chip group into at least two second sub-groups in accordance with distances between center positions of semiconductor chips on the wafers to which the second wafer numbers have been assigned and center positions of the wafers, selecting at least three semiconductor chips from the second sub-groups, further selecting a chip including the center position of the wafer inside thereof if any, and assigning a chip number to the selected semiconductor chip;

producing a lattice to divide a region in the selected semiconductor chip to which the chip number is assigned into rectangular regions the number of which exceeds the number of regions of at least two rows and two columns, on the basis of in-chip coordinates, selecting at least four lattice points from the lattice points of the lattice, selecting a pattern in the vicinity of the selected lattice points from the pattern formed on the wafer as only one candidate measurement point with respect to the lattice points, and assigning a candidate measurement point number to the candidate measurement point;

defining only some of the candidate measurement points to which the candidate measurement point numbers have been assigned as first measurement points to be actually measured based on a fractional factorial design for each of the respective semiconductor chips to which the chip numbers have been assigned;

preparing a measurement schedule and actually executing measurement to the defined measurement points;

executing an analysis of variance from obtained measurement results on the basis of the fractional factorial design; and changing the measurement schedule on the basis of the result of the analysis of variance.

12. The manufacturing method of a semiconductor device according to claim 11,
wherein said pattern inspection method further comprising:

preparing a measurement schedule and actually executing measurement to the defined measurement points;

executing an analysis of variance from obtained measurement results on the basis of the fractional factorial design; and changing the measurement schedule on the basis of the result of the analysis of variance.

13. A program which allows a computer to implement a method of selecting a pattern to be measured, said selection method comprising:

assigning first wafer numbers in order of a process to a wafer group constituted of a plurality of wafers including a semiconductor chip group respectively, the semiconductor chip group having a plurality of chips, each semiconductor chip having a pattern formed thereon in the process;

dividing the wafer group into at least two first sub-groups in accordance with the first wafer numbers, and selecting at least two wafers having serial first wafer numbers from the first sub-groups to assign second wafer numbers to the selected wafers, respectively;

dividing the semiconductor chip group into at least two second sub-groups in accordance with distances between center positions of semiconductor chips on the wafers to which the second wafer numbers have been assigned and center positions of the wafers, selecting at least three semiconductor chips from the second sub-groups, further selecting a chip including the center position of the wafer inside thereof if any, and assigning a chip number to the selected semiconductor chip;

producing a lattice to divide a region in the selected semiconductor chip to which the chip number is assigned into rectangular regions the number of which exceeds the number of regions of at least two rows and two columns, on the basis of in-chip coordinates, selecting at least four lattice points from the lattice points of the lattice, selecting a pattern in the vicinity of the selected lattice points from the pattern formed on the wafer as only one candidate measurement point with respect to the lattice points, and assigning a candidate measurement point number to the candidate measurement point; and defining only some of the candidate measurement points to which the candidate measurement point numbers have been assigned as first measurement points to be actually measured based on a fractional factorial design for each of the respective semiconductor chips to which the chip numbers have been assigned.

14. A program which allows a computer to implement a pattern inspection method, said pattern inspection method comprising:

assigning first wafer numbers in order of a process to a wafer group constituted of a plurality of wafers including a semiconductor chip group respectively, the semiconductor chip group having a plurality of chips, each semiconductor chip having a pattern formed thereon in the process;

dividing the wafer group into at least two first sub-groups in accordance with the first wafer numbers, and selecting at least two wafers having serial first wafer numbers from the first sub-groups to assign second wafer numbers to the selected wafers, respectively;

dividing the semiconductor chip group into at least two second sub-groups in accordance with distances between center positions of semiconductor chips on the wafers to which the second wafer numbers have been assigned and center positions of the wafers, selecting at least three semiconductor chips from the second sub-groups, further selecting a chip including the center position of the wafer inside thereof if any, and assigning a chip number to the selected semiconductor chip;

producing a lattice to divide a region in the selected semiconductor chip to which the chip number is assigned into rectangular regions the number of which exceeds the number of regions of at least two rows and two columns, on the basis of in-chip coordinates, selecting at least four lattice points from the lattice points of the lattice, selecting a pattern in the vicinity of the selected lattice points from the pattern formed on the wafer as only one candidate measurement point with respect to the lattice points, and assigning a candidate measurement point number to the candidate measurement point;

defining only some of the candidate measurement points to which the candidate measurement point numbers have been assigned as first measurement points to be actually measured based on a fractional factorial design for each of the respective semiconductor chips to which the chip numbers have been assigned;

preparing a measurement schedule and actually executing measurement to the defined measurement points;

executing an analysis of variance from obtained measurement results on the basis of the fractional factorial design; and changing the measurement schedule on the basis of the result of the analysis of variance.

15. A pattern inspection apparatus which is capable to communicate with an external inspection device and which prepares a schedule to measure a pattern to supply the prepared measurement schedule to the external inspection device, said pattern inspection apparatus comprising:

a controller which receives information of a measurement point defined as a point to be actually measured to prepare a measurement schedule and supplies a first command signal to execute measurement to the defined measurement point to the external inspection device, the measurement point being defined by:

assigning first wafer numbers in order of a process with respect to a wafer group constituted of a plurality of wafers including semiconductor chip groups in which patterns are formed by a fine processing process;

dividing the wafer group into at least two first sub-groups in accordance with the first wafer numbers, and selecting at least two or more wafers having serial first wafer numbers from the first sub-group to assign second wafer numbers;

dividing the semiconductor chip group into at least two second sub-groups in accordance with distances between center positions of semiconductor chips on the wafers to which the second wafer numbers have been assigned and center positions of the wafers, selecting at least three semiconductor chips from the second sub-group, further selecting a chip including the center position of the wafer inside if any, and assigning a chip number to the selected semiconductor chip;

producing a lattice to divide a region in the selected semiconductor chip to which the chip number is assigned into rectangular regions exceeding a quantity of at least two rows and two columns based on in-chip coordinates, selecting at least four lattice points from the lattice points of the lattice, selecting a pattern in the vicinity of the selected lattice points in the pattern formed on the wafer as only one candidate measurement point with respect to the lattice point, and assigning a candidate measurement point number to the candidate measurement point; and selecting only some of the candidate measurement points to which the candidate measurement point numbers have been assigned based on a fractional factorial design with respect to the respective semiconductor chips to which the chip numbers have been assigned.

16. The pattern inspection apparatus according to claim 15, further comprising:

a calculator which receives information of a measurement result from the external inspection device, and executes an analysis of variance on the basis of the fractional factorial design, wherein the controller changes the measurement schedule on the basis of the result of the analysis of variance and transmits a second command signal to execute measurement in accordance with the changed measurement schedule to the external inspection device.

17. The pattern inspection apparatus according to claim 16, wherein the controller omits some of the defined measurement points on the basis of the result of the analysis of variance and defines new measurement points to change the measurement schedule.

18. The pattern inspection apparatus according to claim 15, wherein the controller transmits a third command signal to the external inspection device to measure a standard pattern prepared beforehand a predetermined times, prior to the transmission of the first command signal, and evaluates reliability of the external measurement device on the basis of the measurement result supplied from the external inspection device.

19. The pattern inspection apparatus according to claim 18,
wherein the controller determines the number of times of measurement to the measurement points, when the result of the evaluation of the reliability of the external measurement device is lower than a predetermined standard value, produces and transmits a fourth command signal to the external inspection device to repeat the measurement to the measurement points the determined number of measurement times, and adopts an average value of the measurement results from the external inspection device which has executed inspection in response to the fourth command signal as a measured value of each measurement point.

20. The pattern inspection apparatus according to claim 15, further comprising:
a terminal device which receives information of the result of the analysis of variance from the controller to process the information into visible information of a table or a graph; and
a display which displays the information of the table or the graph.

* * * * *